United States Patent
Liu et al.

(10) Patent No.: US 8,462,326 B2
(45) Date of Patent: Jun. 11, 2013

(54) SCHLIEREN TYPE ULTRASONIC WAVE OBSERVER SYSTEM

(75) Inventors: Hao-Li Liu, Taoyuan County (TW); Chung-Cheng Kung, Tainan (TW); Ting-Chia Chang, Taipei (TW)

(73) Assignee: Chang Gung University, Tao-Yuan (TW)

( * ) Notice: Subject to any disclaimer, the term of this patent is extended or adjusted under 35 U.S.C. 154(b) by 221 days.

(21) Appl. No.: 12/929,219

(22) Filed: Jan. 10, 2011

(65) Prior Publication Data

US 2012/0113430 A1     May 10, 2012

(30) Foreign Application Priority Data

Nov. 5, 2010 (TW) ............................... 99133772 A

(51) Int. Cl.
*G01N 21/41* (2006.01)
*G01J 3/45* (2006.01)

(52) U.S. Cl.
USPC ............ 356/129; 356/134; 356/135; 356/456

(58) Field of Classification Search
USPC .................... 356/128–137; 73/1.83, 606, 602
See application file for complete search history.

(56) References Cited

U.S. PATENT DOCUMENTS

| | | | | |
|---|---|---|---|---|
| 2,832,214 | A | * | 4/1958 | Trommler ........................ 73/606 |
| 3,836,950 | A | * | 9/1974 | Bhuta et al. ..................... 73/608 |
| 3,890,829 | A | * | 6/1975 | Korpel et al. ................... 73/604 |
| 4,012,951 | A | * | 3/1977 | Kessler ............................ 73/606 |
| 4,174,634 | A | * | 11/1979 | Dory .............................. 73/606 |
| 4,426,134 | A | * | 1/1984 | Abramovitz et al. ......... 359/306 |
| 4,463,608 | A | * | 8/1984 | Takeuchi et al. ................ 73/606 |
| 4,518,992 | A | * | 5/1985 | Kessler et al. ................. 348/163 |
| 5,463,593 | A | * | 10/1995 | Zanelli et al. .................... 367/13 |
| 2010/0122566 | A1 | * | 5/2010 | Kim ................................ 73/1.82 |

\* cited by examiner

*Primary Examiner* — Sang Nguyen
(74) *Attorney, Agent, or Firm* — Bacon & Thomas, PLLC

(57) ABSTRACT

The invention discloses the Schlieren type ultrasonic wave observer system. The invention states optics interference by the ultrasonic wave sound field after perturbation the medium, and combines to make the interference penetration optical projection the image, the goal lies in the observation ordinary naked eye blind ultrasonic wave sound field distribution. Characteristic of the invention using the spectroscope and the reflector combination, as well as microcontroller precise time delay control, might formerly be limited under the 4F optical field length limit to enhance largely the field of vision the several fold.

3 Claims, 14 Drawing Sheets

SCHLIEREN TYPE ULTRASONIC WAVE OBSERVER SYSTEM

BACKGROUND OF THE INVENTION

1. Field of the Invention

The invention relates to a Schlieren type ultrasonic wave observer system, particularly to a Schlieren type ultrasonic wave optical observer system.

2. Description of the Prior Art

The Schlieren phenomenon was found by the U.K. inventor (Robert Hooke) first in 1665. Afterward the German scientist (August Joseph Ignaz Toepler) manufactured the first Schlieren photography apparatus in the world.

As for the technological principle of so-called Schlieren photography apparatus, because the light pierces through the transparent medium with uneven density, the advance direction of pierced light beam will be refracted due to the refractive index of transparent medium is changed with density. Thus, the Schlieren photography apparatus utilizes the perturbation of fluid on the light wave to present the geometrical shape and concentration at the place with uneven density by the optical observation. It is able to convert the change of flow field unable to be seen by ordinary naked eye into visible image. Therefore, it is able to take the picture for shape of invisible air flow (or water flow). It is also able to observe the wave characteristics or change of hot air conduction through different medium, such as liquid, gas or solid.

As shown in FIG. 1, the conventional optical system with Schlieren photography apparatus normally comprises an adjustable knife edge, a lamp type light source and a set of lens, in order to observe the image directly. However, due to too many optical components and the limitation of lens focus, the system will be bulky and unfavorable to be carried. The optical components are very expensive, and it is very difficult to be made. Thus, the price can not be born generally, and the bigger lens is often unable to be customized. Thus, the vision of generated image will be limited, and full ultrasonic wave image will be unable to be obtained in a time.

FIG. 2 shows the conventional space wave filter system (such as optical signal treatment or Fourier transformation system), which is so-called 4-fold (4f) focus system. After the laser is expanded by beam expander, it becomes to the parallel light. After it passes the object plane, the coordinate will be $(x_1, y_1)$ at this moment. The light wave piercing through the object plane will be the object function $f(x_1, y_1)$. When the light wave reaches the rear focus plane (spectrum plane or knife edge) through first lens 1, the spectrum of object function with coordinate (u, v) will be able to be obtained. When the light wave reaches second lens 2, the fully similar image is able to be obtained on the image plane of second lens 2, but its coordinate is reversed completely with coordinate $(x_2, y_2)$. After the coordinate is reversed completely, the same image of original object will be able to be obtained. This system only has an optical field (about 5 cm in diameter). When the full ultrasonic wave sound field is observed, it is necessary to carry out two times of photographing, which will increase the difficulty of photographing.

In the prior art such as U.S. Pat. No. 4,681,437, although a set of optical Schlieren system was established and the technology for installing Schlieren apparatus was proposed, no advanced recommendations were described for the size and application of optical field of vision.

In U.S. Pat. No. 3,847,484, the laser was used as the light source of optical Schlieren system. Compared to other light sources, the laser source is more suitable to be applied in the optical Schlieren system, and it was not necessary to reduce the temperature by the cooling water. The size of optical field and its actual application still were not described.

In U.S. Pat. No. 5,515,158, the reflective focusing type Schlieren system with single lens was established. This Schlieren system employs the mirror reflection line to concentrate the light source. When the light source of this Schlieren system pierces through the field to the reflective grating, a sheet of reflective light can be produced. After the reflective light is returned, it pierces through the flow field to the first lens, and forms the image at its rear again. The design of control and the application of beam expansion field still were not described.

In U.S. Pat. No. 3,582,185, an optical Schlieren system was disclosed. It comprises control system to control the light source and a barrier system. It looks like chess where the arranged mirror surface lies on the light route. The lens had been installed on the light route. Although it could provide a shield system for the image on the light route, and could prevent or allow the passing of light, the optical imaging structure of Schlieren system and the beam expanding way of system still were not described.

In the imaging process of optical system, if a flat pattern is placed at the front focus plane of an ideal lens (Fourier transformation lens), a precise Fourier transformation will be obtained on the rear focus plane of lens, and its spectrum function can be obtained.

It is known from the Fourier spectral theory of electronics, if the spectrum of signal is filtered, the noise of signal can be removed after the signal is recovered. Thus, this Fourier spectral theory can be simulated on the rear focus plane of lens. When the optical grating with different shape and size is placed, the spectrum of pattern can be changed. After the spectrum of pattern is imaged by a second lens, the spectrum of pattern will be treated by the optical signal. The optical grating placed on the rear focus plane of lens is the so-called space filter.

Thus, summarized from the above-mentioned description, the drawbacks of previous art include:
1. The conventional optical Schlieren measurement system is bulky, and it is not portable, thus it is unfavorable for the development of commercialized product.
2. The optical field of vision is limited, thus it is unable to observe the full flow field at a time.
3. When the optical field is expanded, the bigger lens has to be procured. It will increase the manufacturing cost and the difficulty of customization. Thus it is unfavorable for general commercialized development.
4. It is unable to carry out the synchronous time sequence and it does not have the adjustable micro-control single chip core technology.

Therefore, in order to raise the measurement efficiency of optical Schlieren measurement system, carry out the observation of full flow field, and produce more effective ultrasonic wave measurement, it is necessary to develop innovative optical Schlieren measurement technology, so as to raise the efficiency of optical Schlieren measurement system and reduce the research and development time and manufacturing cost.

SUMMARY OF THE INVENTION

The purpose of the invention is to provide a Schlieren type ultrasonic wave observer system, in order to observe the Schlieren and raise the performance of ultrasonic wave measurement.

The optical sound field measurement apparatus of the invention comprises a continuous wave laser, optical lens, water tank, space filter, charge-coupled device, and computer.

As for the design of light route, the invention uses the optical field focusing lens to form the image on the charge-coupled device directly. Thus, the secondary imaging via lens is not required, the optical signal can be increased, and the Schlieren comparison of sound field will be more obvious.

In the whole optical structure, the invention uses the setup angle and match of spectroscope and reflector to increase the optical field of vision by several folds. It even is able to increase the quantity of spectroscopes to expand the vision of optical field infinitely in accordance with the actual requirement.

The beam expansion optical field of the invention adopts the spectroscope and the reflector, which can reduce the whole cost, and can benefit the commercialized development.

A quartz glass with 45° angle is installed in the water tank of the invention, which can change the advance route of ultrasonic wave to become the direction of ultrasonic wave axle. Thus, it can observe the wavelength of ultrasonic wave and the precise position of the focus.

The optical unit and ultrasonic wave control unit of the invention are connected by single chip microcontroller to become the control core, and use single chip microcontroller to adjust the delay time, in order to achieve the precise effect with respect to light velocity and sound velocity synchronously.

When the invention is used to observe the wave propagation of ultrasonic wave, the focusing state of Schlieren in ultrasonic wave sound field can be observed, and the auxiliary propagation of image information can be carry out.

The characteristic of the invention is to use the spectroscope and the reflector combination to control precise time delay of single chip. It is able to increase the field of vision by several folds under the limit of conventional 4F optical field length.

The invention is suitable to collect full ultrasonic wave focusing information, thus it is favorable to observe the sound field distribution after the ultrasonic wave piercing through the foreign object (such as skull, rib, biological tissue). When the ultrasonic wave is piercing through the foreign object, if the focusing position can be observed in advance, the accuracy of thermal treatment position can be increased.

Therefore, the advantage and spirit of the invention can be understood further by the following detail description of invention and attached figures.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

The invention relates to a Schlieren type ultrasonic wave observer system and application method thereof, and further increase the measurement efficiency.

Figure 1:
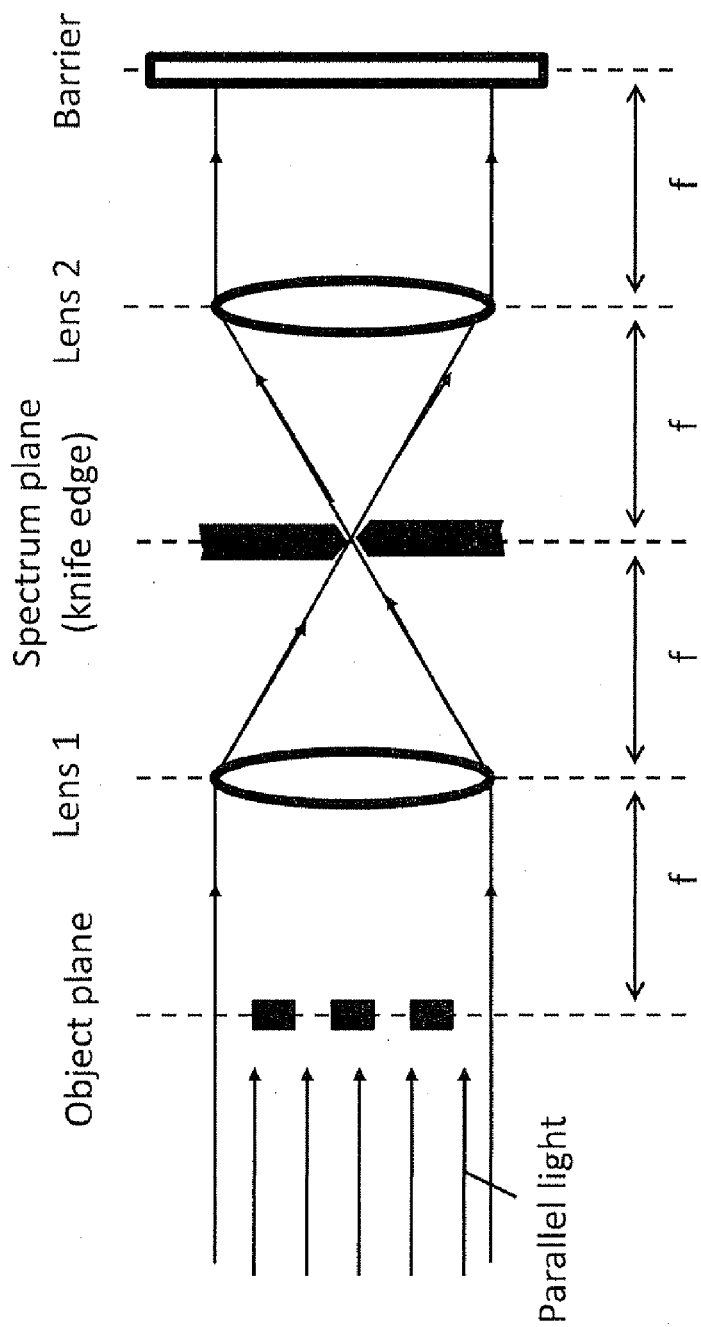
FIG. 1 is a graph illustrating the conventional optical system with Schlieren photography apparatus.
Figure 2:
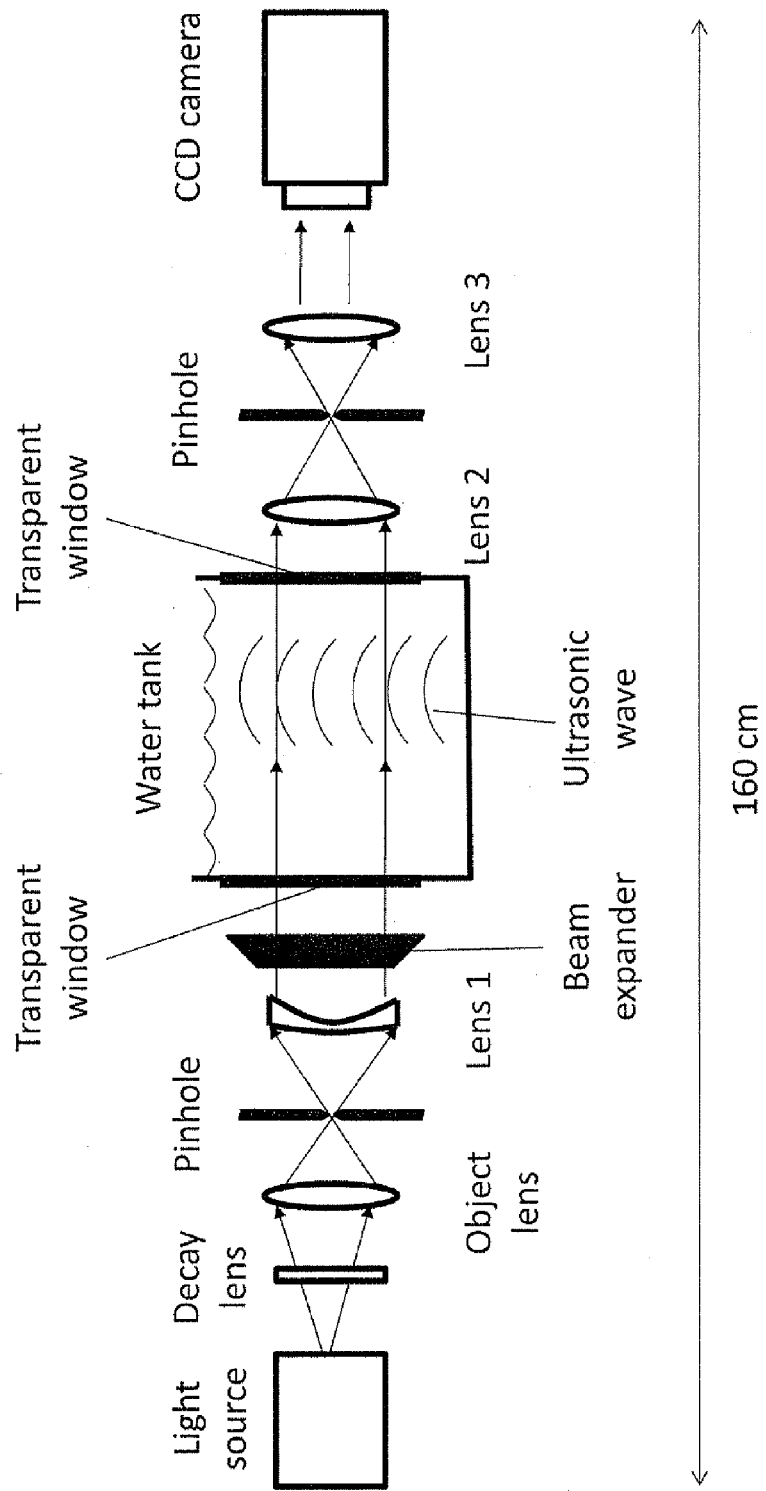
FIG. 2 is a graph illustrating the conventional space wave filter system.
Figure 3:
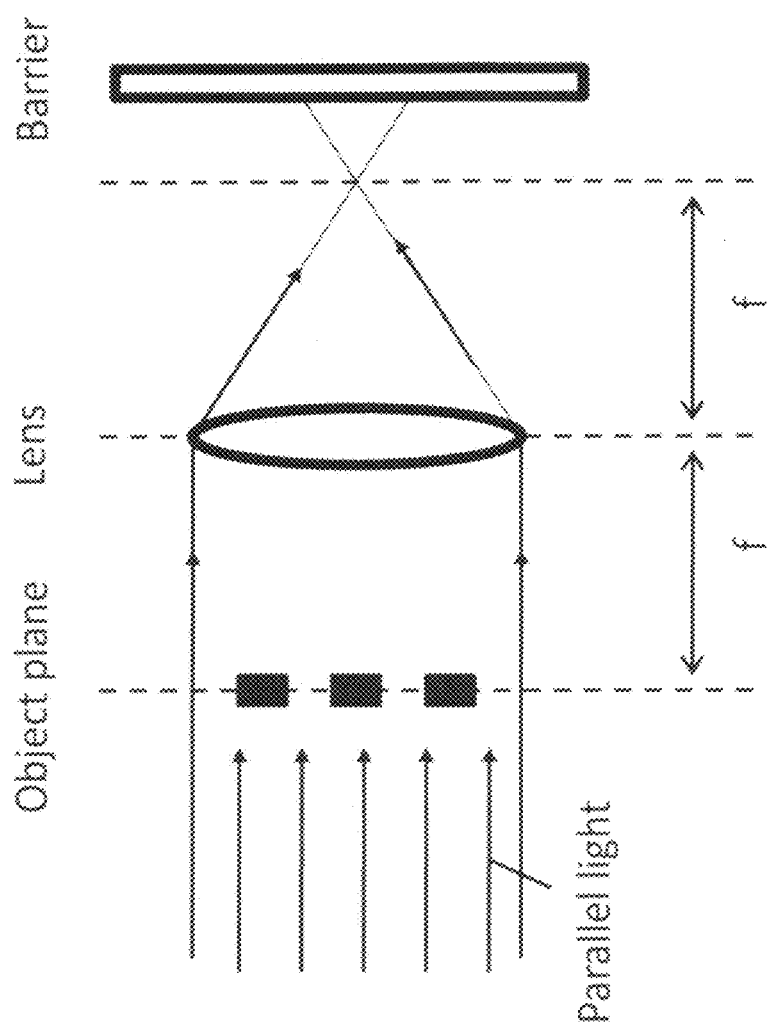
FIG. 3 is a graph illustrating the principle of 3-fold focus (3F) system of the invention.

FIG. 3 shows the principle of 3-fold focus (3F) system of the invention. The system can use 3-fold focus to show the Schlieren effect, even have stronger image contrast. As shown in FIG. 3, the invention uses the space filter and beam expander to disperse the laser beam into the parallel light. After the parallel light pierces the object plane, the 1-fold focus is obtained. When the collected image is converged by a lens, the 2-fold focus is obtained. Finally, when the focusing image is shown on the barrier, the 3-fold focus is obtained.

Figure 4:
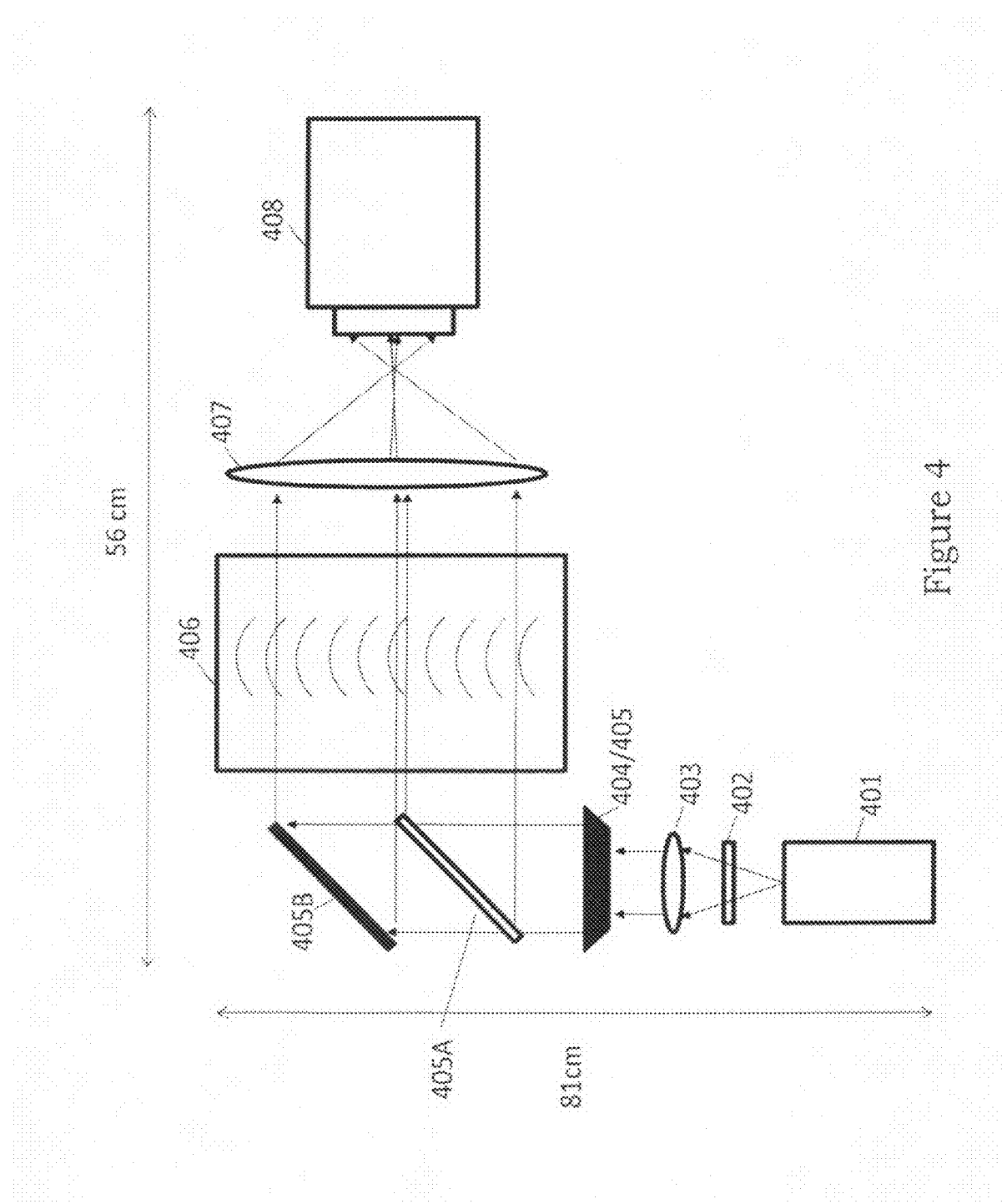
FIG. 4 is a graph illustrating the optical part for the Schlieren type ultrasonic wave observer system of the invention.

FIG. 4 shows the optical part for the Schlieren type ultrasonic wave observer system of the invention. It comprises a continuous wave laser 401, followed by decay lens 402, objective lens 403, pinhole 404 (the objective lens 403 and pinhole 404 can be combined to the so-called space filter), beam expander 405, water tank 406, optical lens 407, charge-coupled device (CCD) 408 and computer 409.

FIG. 4 still shows the optical part for the Schlieren type ultrasonic wave observer system of the invention. The relevant position of sequence is arranged from the continuous wave laser 401 to decay lens 402, objective lens 403, pinhole 404, beam expander 405, water tank 406, optical lens 407, charge-coupled device (CCD) 408 and computer 409.

As shown in FIG. 4, the retrieved image is the cluster wave. When the image is retrieved, it is necessary to use the ultrasonic wave, laser, and camera simultaneously. Due to the sound speed of ultrasonic wave is 1480 m/s in the water and the light speed is 299,792,458 m/s, it is necessary to delay the photographing time of laser and camera, in order to retrieve the image. As for the system control, the computer software LabVIEW is used to set up the remote control system (GUI). All components use the interface bus (GPIB) and RS-232 (EIA-RS-232) serial data communication interface standard as the connection mechanism, which includes the frequency setup for the signal required by ultrasonic wave probe, the amplifying rate of radio frequency amplifier, and the monitor for the output power of power meter. Thus the output result can be monitored and the original image signal can be retrieved in time.

FIG. 4 still shows the optical part for the Schlieren type ultrasonic wave observer system of the invention. After the light beam is emitted from the continuous wave laser 401, it becomes a parallel light by passing through the decay lens 402 and the plano-convex lens 403. The parallel light enters beam expander 405 through the pinhole 404 (the objective lens 403 and pinhole 404 can be combined to the so-called space filter). The beam expander 405 expands the parallel light into an approximate 5-cm parallel optical field. After the parallel optical field passes through the spectroscope 405A of beam expander 405, it is dispersed into a piercing parallel light beam and a reflecting parallel light beam. After the piercing parallel optical field is reflected by the reflector 405B of beam expander 405, it parallels to the previous reflecting parallel light beam. Both light sources are tangent without overlap, which forms an inverse "8" shape optical field in the water tank 406. The inversed 8 shape optical field pierces through the water tank 406. The collected image is converged by the plano-convex lens 407 on the charge-coupled device 408, and is sent to the computer 409 for display. The invention not only can magnify the optical field, but also can turn the light route, in order to reduce the design of whole body. It is designed to let a parallel light piercing through the object to get the projected image. The collected image is converged by the plano-convex lens on the charge-coupled device 408. The virtual image at the rear of focus will be shown on the computer 409 via the charge-coupled device 408.

Figure 5:
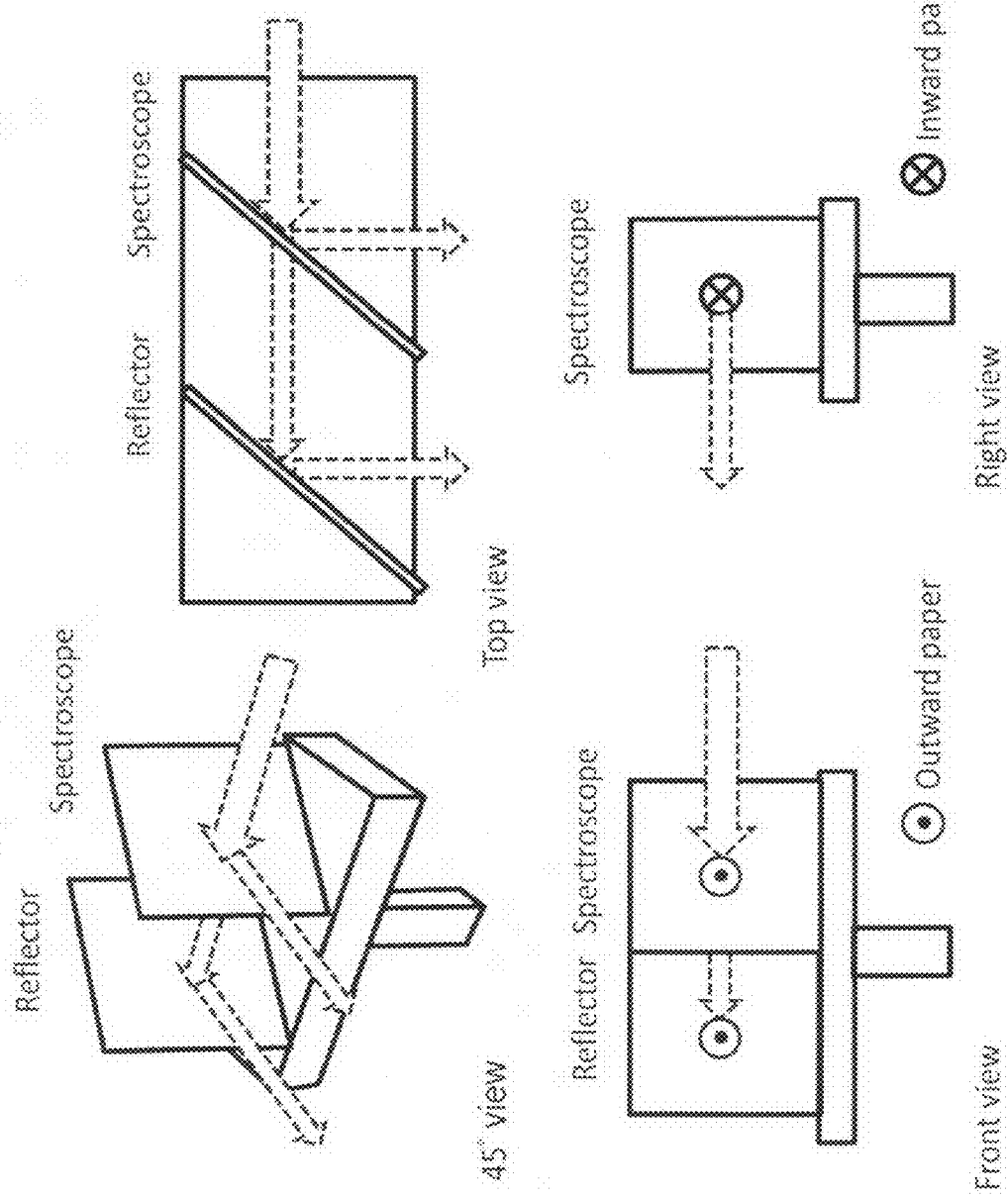
FIG. 5 is a graph illustrating the operation principle of beam expander.

FIG. 5 shows the operation principle of the invented beam expander (including 405A and 405B). It comprises the front view angle, the up view angle, right view angle and 45° view angle etc. The setup angle and match of spectroscope 405A and reflector 405B are used to increase the optical field of vision by several folds. Due to the spectroscope 405A can divide the light into two light routes evenly, this feature can be used to divide the optical field of single light into two light routes in 45° angle (the angle can be controlled in accordance with the requirement) evenly. Due to the incidence angle equals to the emergence angle, when the incidence angle is 45°, the light will be emitted at 45°, thus the light route can be turned by 90°. When the reflector 405B is placed at 45°, the light route can be converted into a same optical field with parallel light route. When the orthographic projections of spectroscope 405A and reflector 405B are tangent, both separated optical fields can be as close as possible, in order to form an inverse 8 shape magnified optical field. A plurality of spectroscopes can be used to expand the optical field infinitely.

Figure 6:
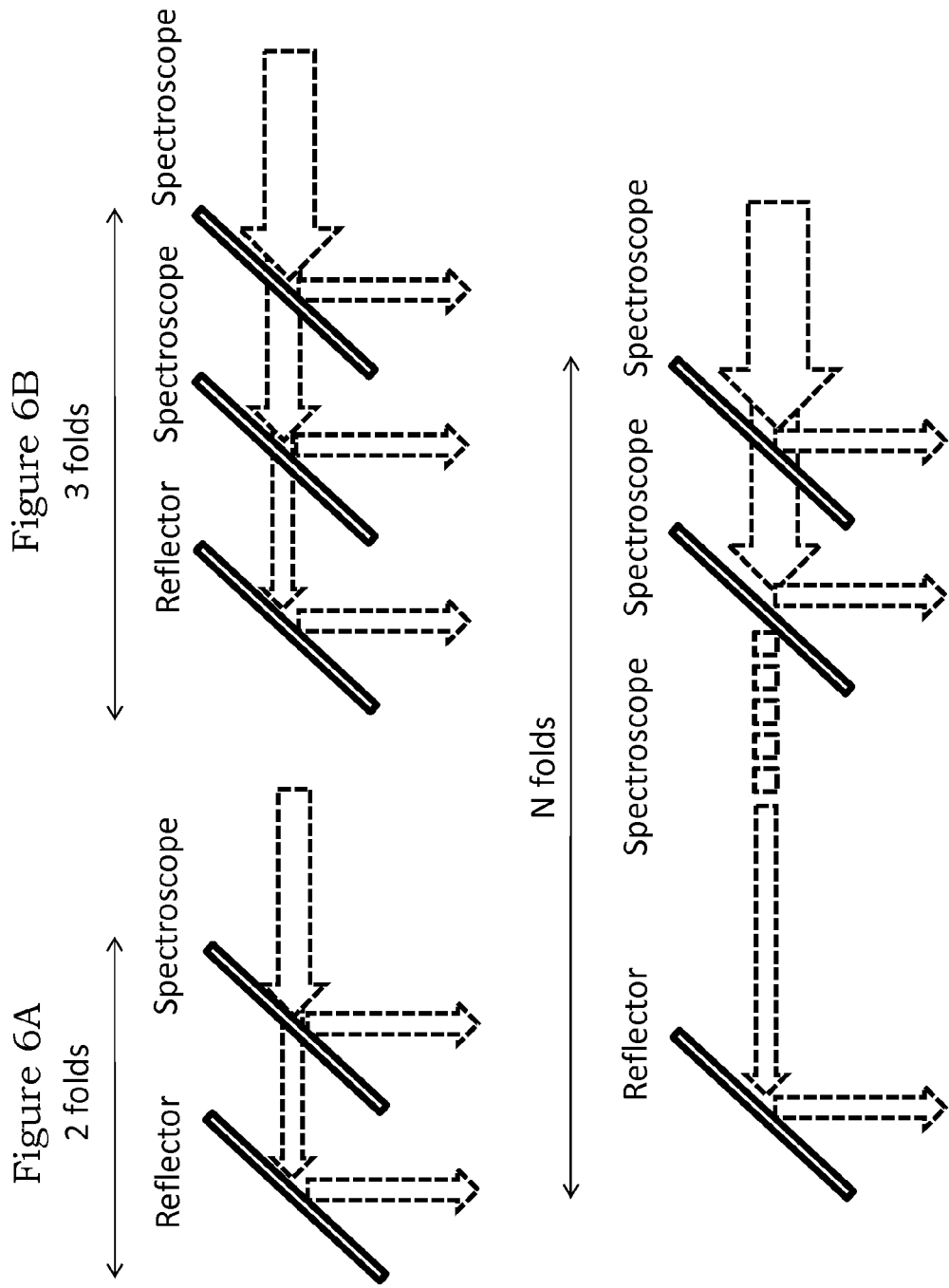
FIG. 6A is a graph illustrating the 2F beam expander.
FIG. 6B is a graph illustrating the 3F beam expander.
FIG. 6C is a graph illustrating the NF beam expander.

As the 2F beam expander shown in FIG. 6A (referring to the beam expander (including 405A and 405B) in FIG. 4), when a spectroscope and a reflector are used, the light beam can be expanded to 2 folds. In FIG. 6B, as the 3F beam expander shows when two spectroscopes and a reflector are used, the light beam can be expanded to 3 folds. As the NF beam expander is shown in FIG. 6C, when N−1 spectroscopes and a reflector are used, the light beam can be expanded to N folds. The beam expander of the invention can be used to expand the optical field. It can reduce the photographing time of the second shift and reduce the cost. The full "ultrasonic wave Schlieren" image can be observed at a time.

Figure 7:
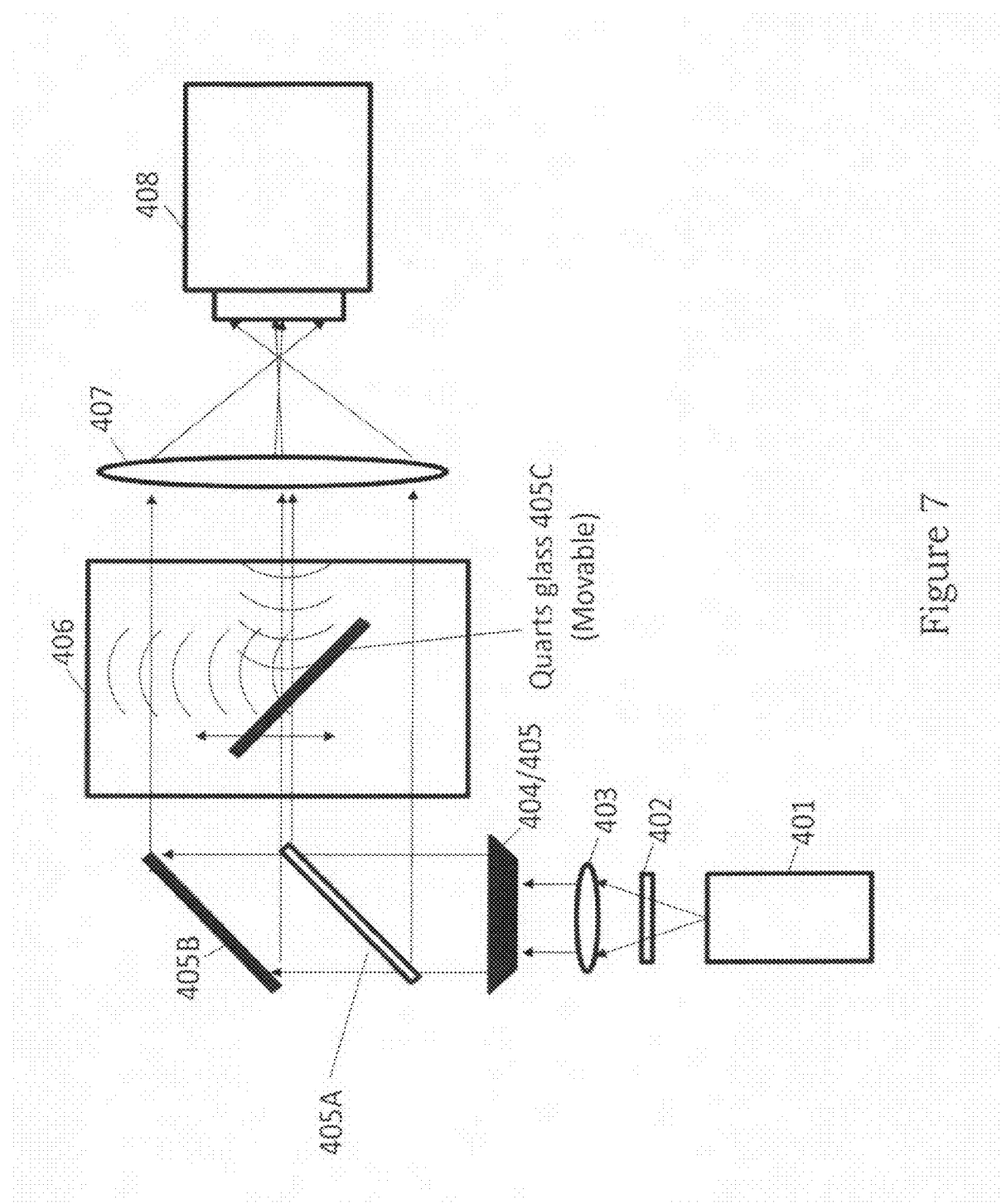
FIG. 7 is a graph illustrating the observation of wavelength and focus at the ultrasonic axle direction.

FIG. 7 is a graph illustrating the observation of wavelength and focus at the ultrasonic axle direction. In the ultrasonic sound field, a quartz glass 405C with 45° angle is installed in the water tank 406. The used principle and physical definition is that the incidence angle equals to the emergence angle. The light route of ultrasonic wave can be turned by 90°, in order to parallel to the ultrasonic wave axle direction of charge-coupled device 408. At this time, the image retrieved by the charge-coupled device 408 is the Schlieren image of the concentric circles (circular distribution of bright and shadow lines).

Figure 8:
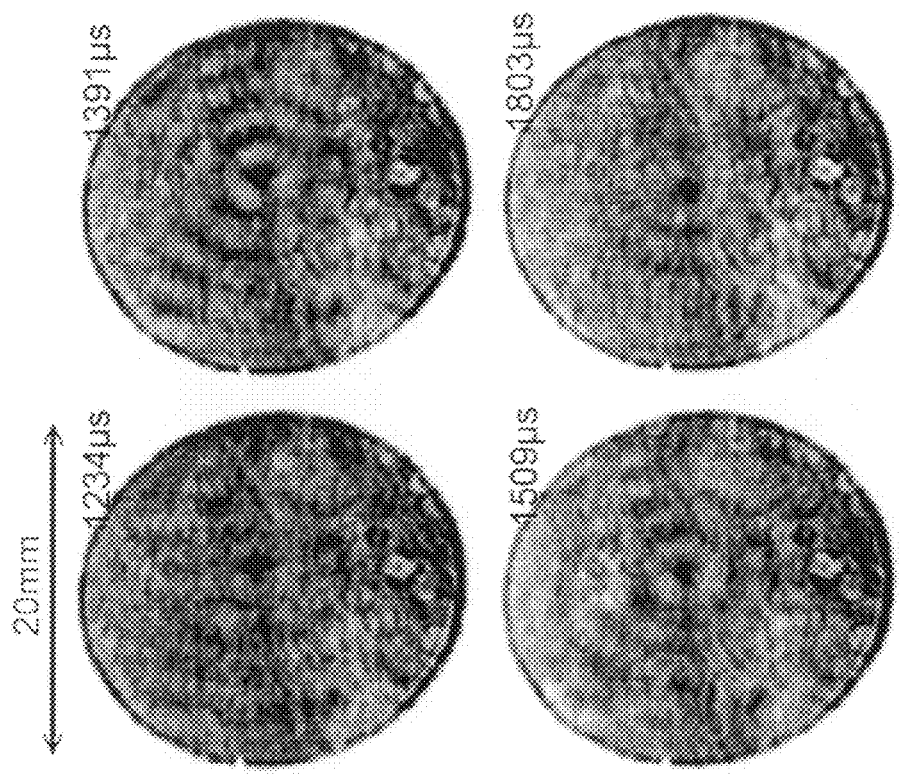
FIG. 8 is a graph illustrating the Schlieren image with concentric circles at the ultrasonic axle direction under different time sequence.

FIG. 8 is a graph illustrating the Schlieren image to observe ultrasonic wave from the transmission direction, where the beam pattern appears to be like concentric circles at the ultrasonic axle direction, and observe beam pattern progression under different time sequence. The central black point is the position of focus, also, the bright line is the wave crest and the shadow line is the wave valley. The distance among the wave crests is 3.75 mm, and then it is calculated to obtain 3.75 mm of wavelength (namely conform to the wavelength of 400 kHz ultrasonic wave). Therefore, the observation method of the invention is suitable to measure the wavelength of ultrasonic wave.

Figure 9:
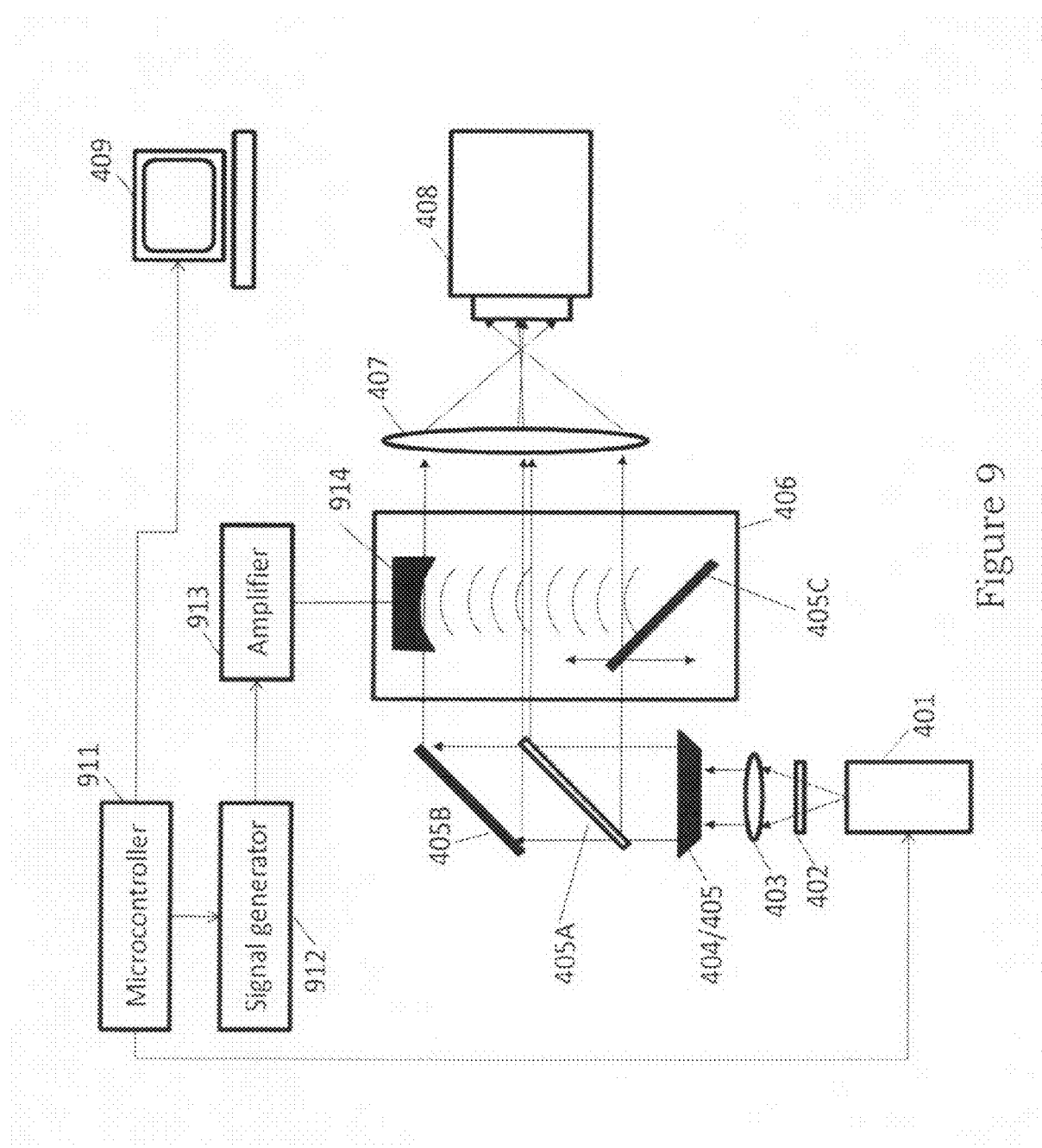
FIG. 9 is a complete graph illustrating a Schlieren type ultrasonic wave observer system of the invention.

FIG. 9 is a complete graph illustrating a Schlieren type ultrasonic wave observer system of the invention. Please refer to FIG. 4 for the optical part of the invention. As shown in this FIG. 9, the optical part of FIG. 4 is included. The computer 409 shown in FIG. 4 connects the single chip microcontroller 911, signal generator 912, amplifier 913, and focusing type ultrasonic wave 914, in order to produce an ultrasonic wave source. The single chip microcontroller 911 connects the continuous wave laser 401 to activate the continuous wave laser 401 directly. In the invention, the computer 409 activates the single chip microcontroller 911, and the single chip microcontroller 911 activates the signal generator 912 and sends the signal to the amplifier 913, in order to amplify it for controlling the focusing ultrasonic wave 914. The single chip microcontroller 911 can transmit the signal to computer 409, in order to control the photographing time of the charge-coupled device 408.

Figure 10:
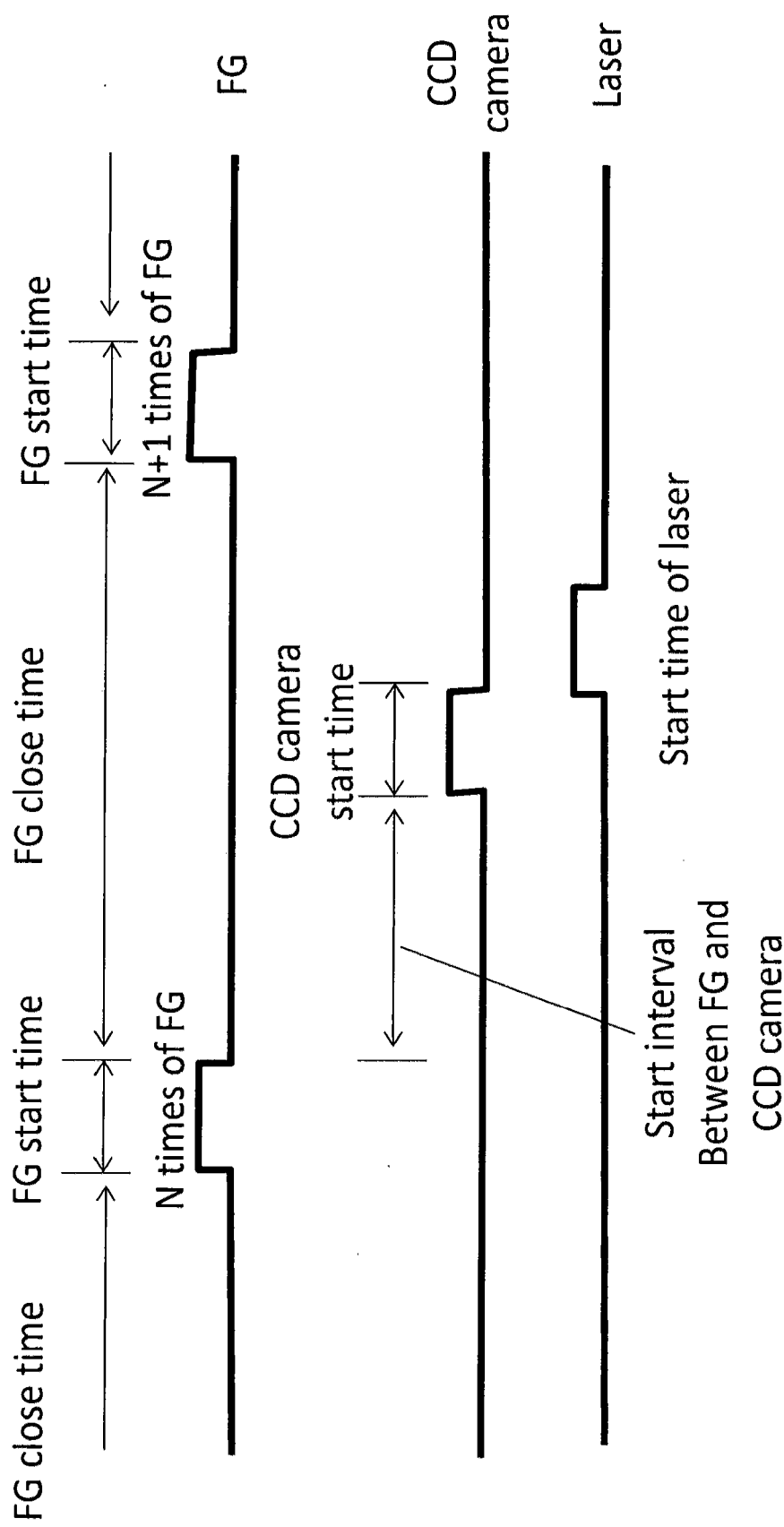
FIG. 10 is a graph illustrating the synchronous delay control apparatus of the invention.

FIG. 10 is a graph illustrating the synchronous delay control method for the Schlieren type ultrasonic wave observer system. The internal cycle of the single chip microcontroller 911 is used to produce the delay signal, in order to control the time sequence. According to the requirement of different instruments, it gives different delay signals. It transmits the delay signals to the computer 409 for carrying on a parameter control, so that the computer 409 only has to choose the first start time (can produce bright and shadow effect) of continuous wave laser 401, the second start time (the position of wave front) of signal generator 912, and the photographing time (with bright and shadow effect) of charge-coupled device 408. The computer 409 uses the graphic interface of Lab-VIEW software to control the parameters of single chip microcontroller, select the function of signal generator 912, and select the gain of power amplifier 913. Thus the invention can photograph the advancing situation of "ultrasonic wave sound field". In the FIG. 10, FG is the signal generator, wherein N is the times for the signal. In order to catch the intact wave, it has to catch a certain signal as the starting point. It is still unable to see the Schlieren from the charge-coupled device 408 at this moment. A small time (4.125 μs) will be increased from the start interval of FG and charge-coupled device 408. Due to the shut off time of FG is constant, thus the start interval of FG and charge-coupled device 408 can determine the position of wave front. Even the cycle can be set for photographing the advancing of wave continuously.

Figure 11:
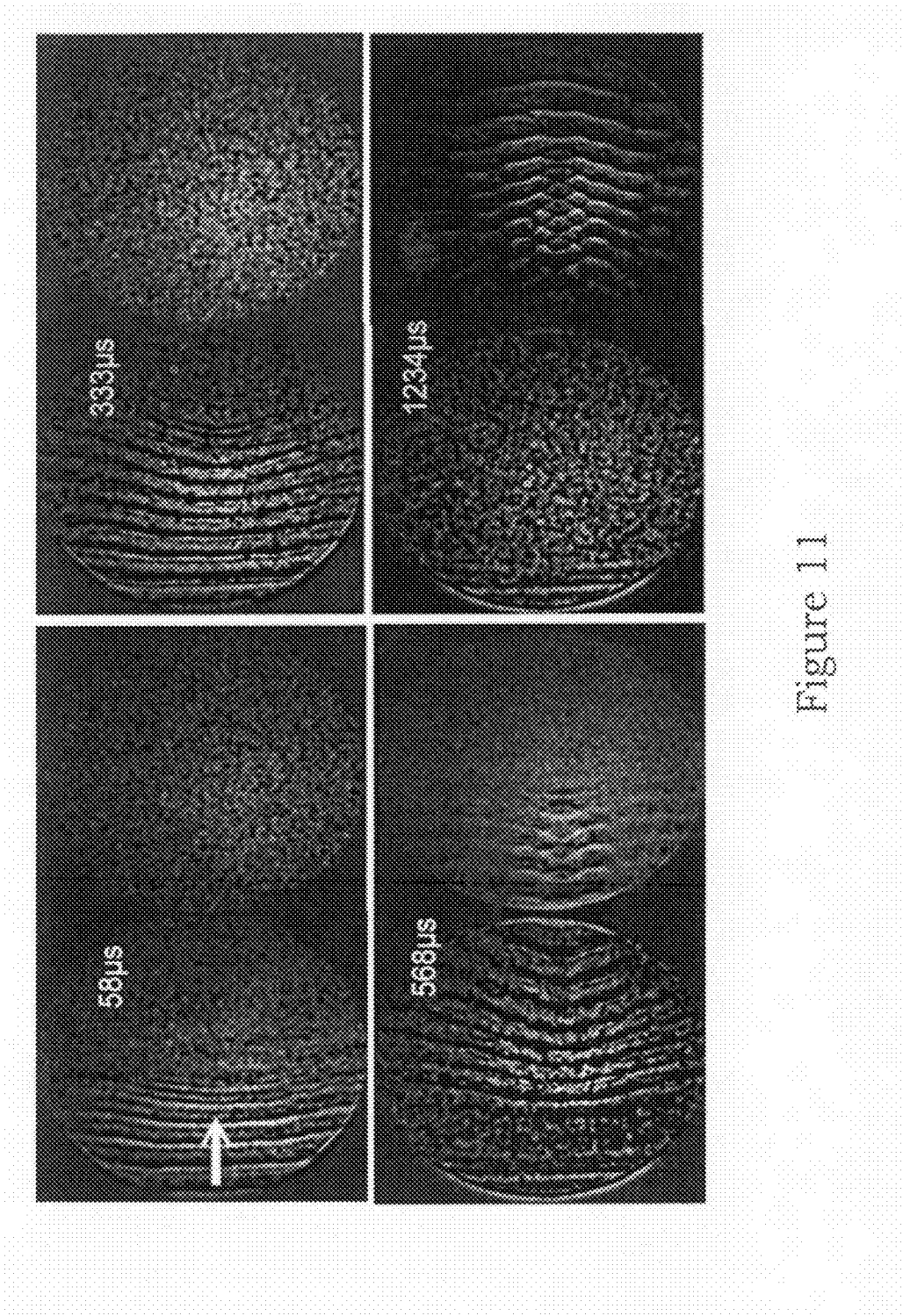
FIG. 11 is a graph illustrating the cluster image of 400 kHz wave.

As for the test results of the invention, the skull with different thickness around the brain chamber of pig is selected as the experiment and test materials. The area is about 35 mm×35 mm. The thickness of skull is 2 mm, 3.5 mm, 6 mm and zero. A 500 mV of peak to peak voltage is supplied by the signal generator. After the power is amplified by the amplifier, the 400 kHz probe of the focusing ultrasonic wave emits the cluster wave. The experimental results are described as follows:

The Schlieren picture (without any pig's skull) in FIG. 11 is the image of 400 kHz cluster wave. It is the image transmitted by the visible wave under the increased time sequence. Its ultrasonic wave is transmitted by the direction of arrow. As for the parameters of the signal generator, 500 mV of peak to peak voltage, 10 cycles, and 500 Hz of Pulse Repetition Frequency (PRF) are set. The delay circuit activates the charge-coupled device 408 to photograph the image per 1.8 μs. The continuous wave laser 401 is opened for 5 μs per 1.8 μs.

Figure 12:
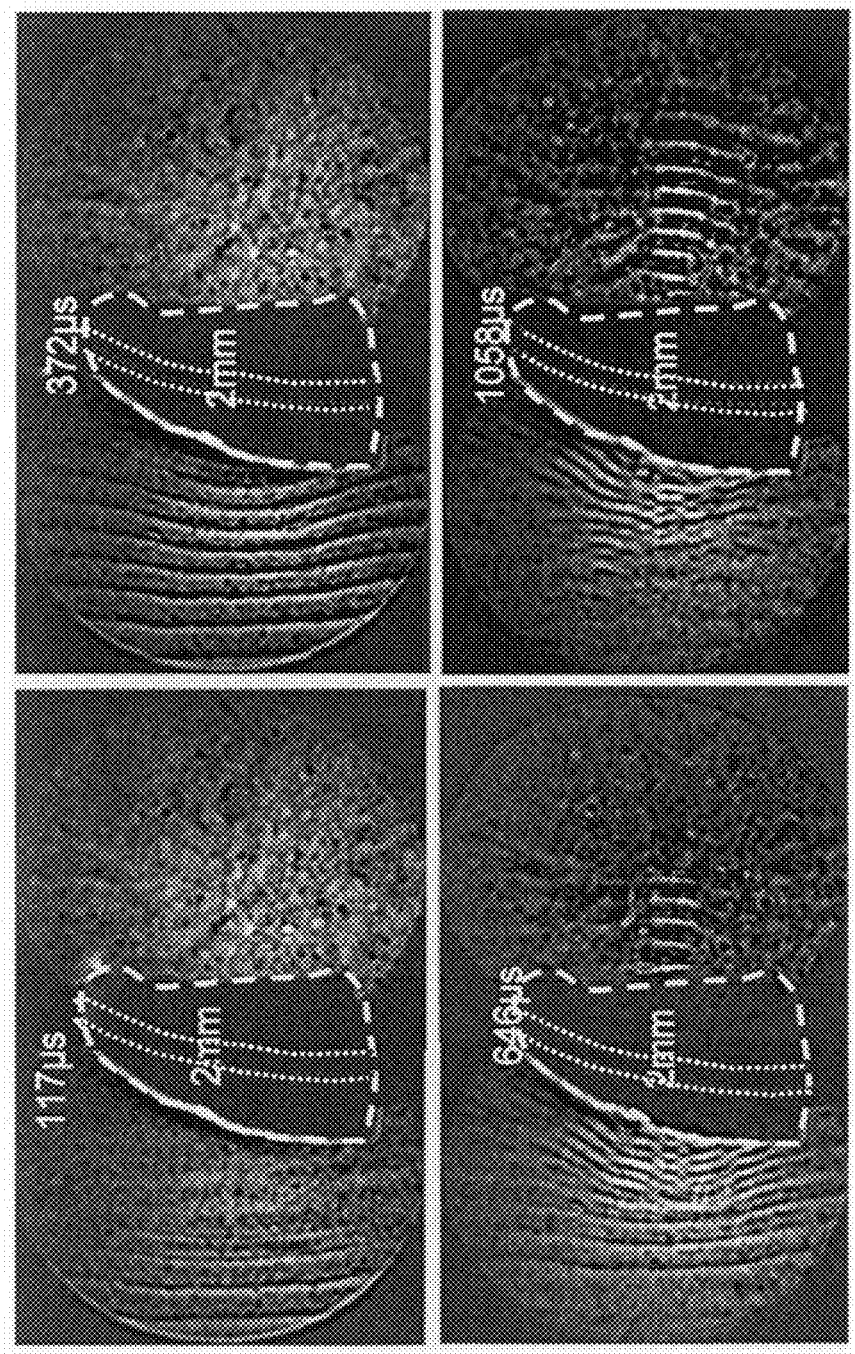
FIG. 12 is a graph illustrating the image for 2 mm thick pig skull compared to FIG. 11.

FIG. 12 shows the image for 2 mm thick pig skull compared to FIG. 11.

Figure 13:
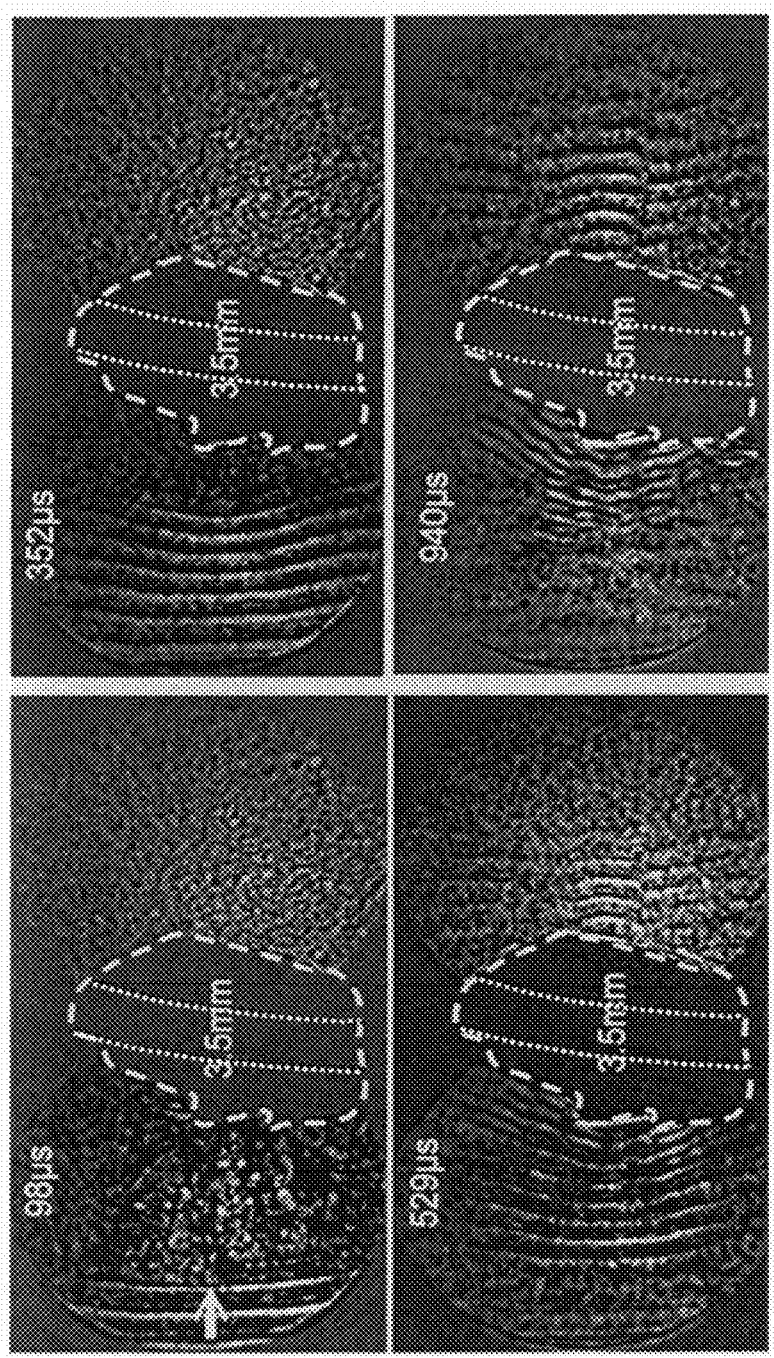
FIG. 13 is a graph illustrating the image for 3.5 mm thick pig skull compared to FIG. 11.

FIG. 13 shows the image for 3.5 mm thick pig skull compared to FIG. 11.

Figure 14:
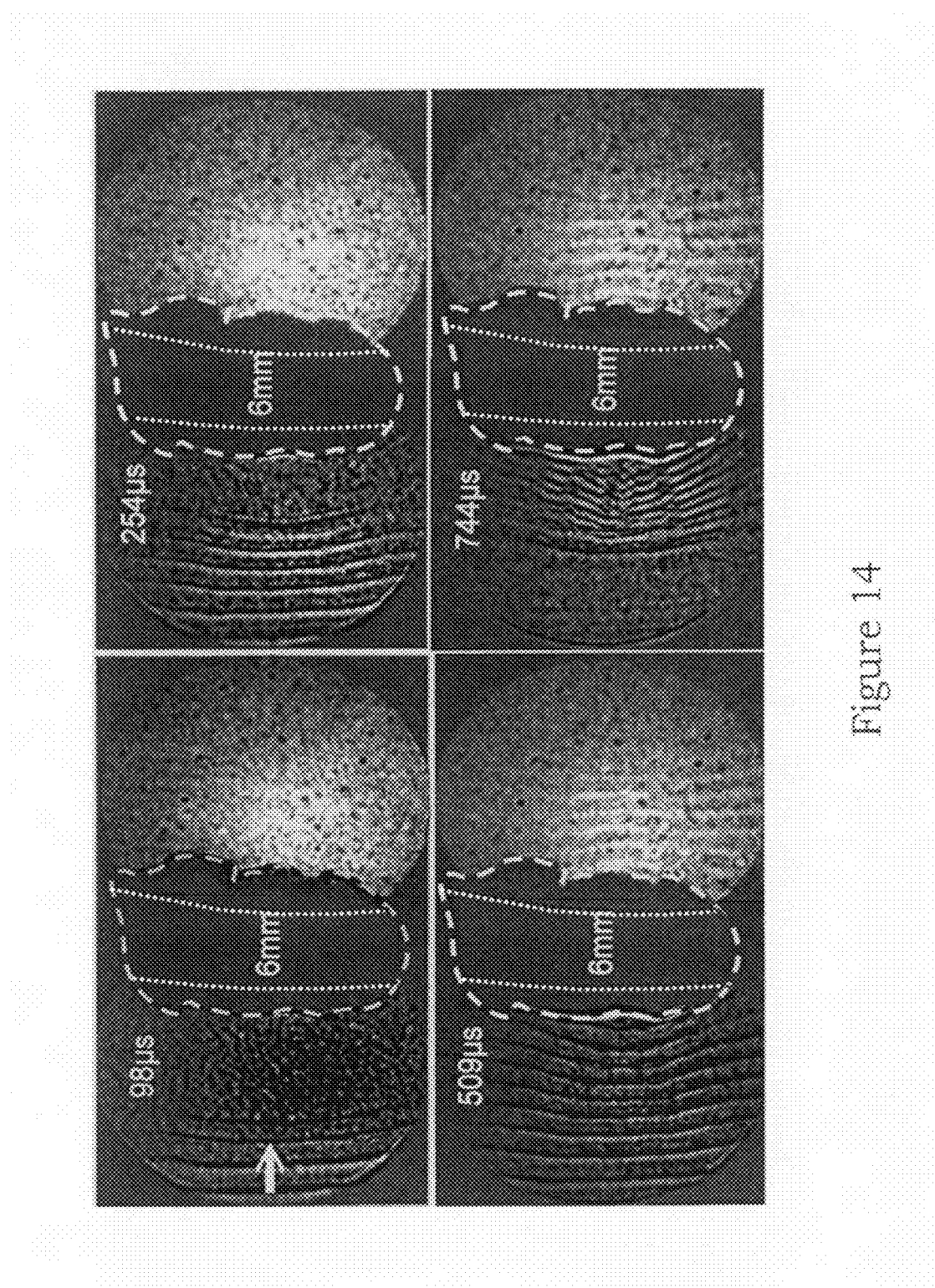
FIG. 14 is a graph illustrating the image for 6 mm thick pig skull compared to FIG. 11.

FIG. 14 shows the image for 6 mm thick pig skull compared to FIG. 11.

In the above-mentioned FIG. 12 to FIG. 14, after the probe is started, it is able to activate the charge-coupled device 408 and the continuous wave laser 401 to take the image per 1.8 μs. From the images, the focus position and pressure distribution of ultrasonic wave sound field, and it is known that the piercing energy sound field will be decreased with the increase of thickness. After the ultrasonic wave is pierced, the focusing position will be changed. Thus, the direction for the change of focusing position can be observed after piercing the skull. The optical field of vision is about 10 cm (a circle with 5 cm in diameter), thus the full advancing direction of ultrasonic wave can be observed completely. From the experimental results, it is known that the "sound field" of Schlieren type ultrasonic wave observer system with 400 kHz focusing ultrasonic wave can observe the focusing or dispersing state effectively after the ultrasonic wave piercing through the heterogeneous substance.

Thus, summarized from the above-mentioned description, as for the optical component system, compared the traditional 4F system and the 3F system of the invention, the 3F system of the invention owns smaller volume. It also has the beam expansion function. The secondary imaging via lens is not required. Thus, the volume, image quality, and photographing time can be improved greatly. The characteristic of the invention is to simplify and combine the ultrasonic wave sound field and the focusing type ultrasonic wave, in order to amplify and expand the limited optical field of vision. It uses single chip microcontroller to control the delay time of light and sound synchronously, in order to photograph the temporary image of the ultrasonic sound field, which can obtain the full ultrasonic wave image completely at a time.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A Schlieren type ultrasonic wave observer system having a 2-fold focus beam expander, comprising:
    a continuous wave laser;
    a computer;
    a microcontroller integrated circuit;
    a signal generator;
    an amplifier;
    a focusing type ultrasonic wave, wherein the computer connects the microcontroller integrated circuit, the signal generator, the amplifier, and the focusing type ultrasonic wave in order to produce an ultrasonic wave source, the microcontroller integrated circuit connecting the continuous wave laser to activate the continuous wave laser directly, the computer activating the microcontroller integrated circuit, and the microcontroller integrated circuit activating the signal generator and sending a signal to the amplifier for controlling the focusing ultrasonic wave;
    a decay lens;
    an objective lens;
    a pinhole;
    a reflector and a spectroscope to form a 2-fold focus (2F) beam expander;
    a water tank, wherein the water tank includes a quartz glass with a 45° angle;
    an optical lens; and
    a charge-coupled device,
    wherein the microcontroller integrated circuit transmits the signal to the computer in order to control a photographing time of the charge-coupled device after a light beam is emitted from the continuous wave laser, the light beam becoming a parallel light by passing through the decay lens and the plano-convex lens, the parallel light entering the beam expander through the pinhole including the objective lens and the pinhole, the beam expander expanding the parallel light into an approximate 5-cm parallel optical field after the parallel optical field passes through the spectroscope of the beam expander, the light beam being dispersed into a piercing parallel light beam and a reflecting parallel light beam after the piercing parallel optical field is reflected by the reflector of the beam expander, the light beam being parallel to a previous reflecting parallel light beam, both light sources being tangent without overlap and forming an inverse "8" shape optical field in the water tank, the inverse 8 shape optical field piercing through the water tank, and the collected image being converged by the plano-convex lens on the charge-coupled device, and sent to the computer for display.

2. A Schlieren type ultrasonic wave observer system having a 2-fold focus beam expander, comprising:
    a continuous wave laser;
    a computer;
    a microcontroller integrated circuit;
    a signal generator;
    an amplifier;
    a focusing type ultrasonic wave, wherein the computer connects the microcontroller integrated circuit, the signal generator, the amplifier, and the focusing type ultrasonic wave in order to produce an ultrasonic wave source, the microcontroller integrated circuit connecting the continuous wave laser to activate the continuous wave laser directly, the computer activating the microcontroller integrated circuit, and the microcontroller integrated circuit activating the signal generator and sending a signal to the amplifier for controlling the focusing ultrasonic wave;
    a decay lens;
    an objective lens;
    a pinhole;
    a reflector and at least two spectroscopes to form at least a 3-fold focus (3F) beam expander;
    a water tank, wherein the water tank includes a quartz glass with a 45° angle;
    an optical lens; and
    a charge-coupled device,
    wherein the microcontroller integrated circuit transmits the signal to the computer in order to control a photographing time of the charge-coupled device after a light beam is emitted from the continuous wave laser, the light beam becoming a parallel light by passing through the decay lens and the plano-convex lens, the parallel light entering the beam expander through the pinhole including the objective lens and the pinhole, the beam expander expanding the parallel light into an approximate 5-cm parallel optical field, after the parallel optical field passes through the spectroscopes of the beam expander, the light beam being dispersed into a piercing parallel light beam and a reflecting parallel light beam after the piercing parallel optical field is reflected by the reflector of the beam expander, the light beam being parallel to a previous reflecting parallel light beam, both light sources being tangent without overlap and forming an inverse "8" shape optical field in the water tank, the inverse 8 shape optical field piercing through the water tank, and the collected image being converged by the plano-convex lens on the charge-coupled device, and sent to the computer for display.

3. The system according to claim 2, wherein a number of the spectroscopes in the beam expander is N−1 and the N−1 spectroscopes form an NF beam expander, where N is bigger than 4.

* * * * *